United States Patent [19]

Bertino et al.

[11] 4,313,887
[45] Feb. 2, 1982

[54] BIS-QUINIZARIN COMPOUNDS

[75] Inventors: Clarence D. Bertino; Robert W. Hill, both of Houston, Tex.; J. Gustav Schulz, Pittsburgh, Pa.

[73] Assignee: Gulf Oil Corporation, Pittsburgh, Pa.

[21] Appl. No.: 201,874

[22] Filed: Oct. 29, 1980

Related U.S. Application Data

[63] Continuation-in-part of Ser. No. 121,547, Feb. 14, 1980, abandoned.

[51] Int. Cl.$^3$ .............................................. C07C 49/74
[52] U.S. Cl. ................................................... 260/367
[58] Field of Search ......................................... 260/367

[56] References Cited

U.S. PATENT DOCUMENTS 1,867,858  7/1932  Mieq .................................... 260/367

OTHER PUBLICATIONS

*Das Anthracen and die Anthraquinone* p. 540, Dr. J. Houben, 1929, Georg Thiemel Verlagl Leipzig.

*Primary Examiner*—Winston A. Douglas
*Assistant Examiner*—Raymond Covington
*Attorney, Agent, or Firm*—Richard L. Kelly

[57] ABSTRACT

Bis-quinizarin compounds are disclosed. They have the structure:

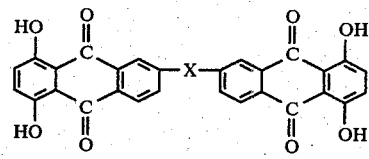

where X is

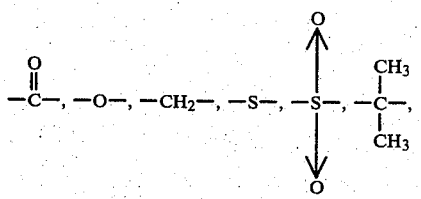

—$CF_2$—, or a bond.

4 Claims, No Drawings

BIS-QUINIZARIN COMPOUNDS

CROSS REFERENCE TO RELATED APPLICATION

This application is a continuation-in-part to our earlier application Ser. No. 121,547, filed on Feb. 14, 1980, now abandoned.

BACKGROUND OF THE INVENTION (a) Field of the Invention

The invention relates to certain bis-quinizarin compounds and methods for their preparation.

(b) Description of the Prior Art

Quinizarin is a known compound whose synthesis is reported in *Organic Synthesis, Collective Volume I,* page 476. To the best of the applicants' knowledge, bis-quinizarin compounds are not reported in the literature.

SUMMARY OF THE INVENTION

The products of the invention are bis-quinizarin compounds having the structure:

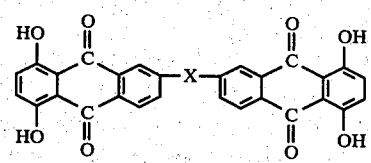

where X is

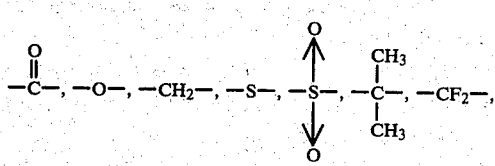

or a bond. The preferred product of the invention is 6,6'-carbonyl bis-quinizarin which has the structure:

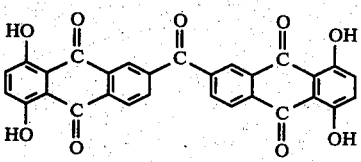

The invention also includes a process for preparing bis-quinizarin compounds in which an aromatic tetracarboxylic acid dianhydride and p-chlorophenol, in critical molar portions, are reacted together in oleum having boric acid dissolved therein.

DETAILED DESCRIPTION OF THE INVENTION

The bis-quinizarin compounds are prepared by reacting p-chlorophenol with an aromatic tetracarboxylic acid dianhydride having the structure:

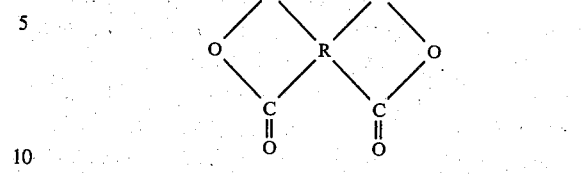

where R has the structure:

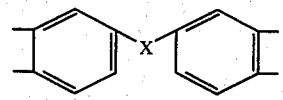

where X is

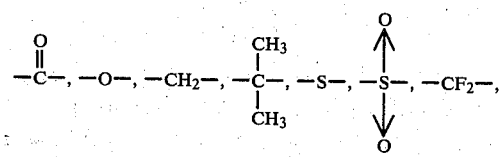

or a bond. Examples of suitable compounds include 3,3',4,4'-benzophenonetetracarboxylic acid dianhydride (BTDA),3,3',4,4'-biphenyl tetracarboxylic acid dianhydride, 2,2-bis(3,4-dicarboxyphenyl)propane dianhydride, bis(3,4-dicarbyxyphenyl)ether dianhydride, naphthalene-2,3,6,7-tetracarboxylic acid dianhydride, bis(3,4-dicarboxyphenyl)methane dianhydride, bis(3,4-dicarboxyphenyl)sulfone dianhydride, and the like. Such compounds are known and reported in the art.

The p-chlorophenol and the dianhydride, in molar portions subsequently described, together with boric acid are heated in oleum to a temperature of at least 175° C. to form the desired bis-quinarizin compound.

Stoichiometric considerations require that 2 moles of the p-chlorophenol react with 1 mole of the dianhydride. It has been observed that the formation of undesired by-products is minimized by employing an excess of the dianhydride. It is preferred to employ only 1.1 to 1.9 and more especially 1.4–1.8 molar portions of the p-chlorophenol for each molar portion of the dianhydride. Boric acid plays a role in the reaction and should be employed in an amount at least molarly equivalent to the p-chlorophenol.

Oleum is the reaction solvent employed and should contain at least about 10 weight % of $SO_3$. Larger excesses of $SO_3$ can be employed but are not required. When commercial grade 98% concentrated sulfuric acid is employed as the reaction solvent, additional incompletely identified co-products are formed which are difficult to separate from the desired bis-quinizarin product. Although the quantity of oleum employed is not critical, it is preferred to employ at least 2 and preferably at least 4 parts by weight of oleum for each part of combined weight of p-chlorophenol and dianhydride.

The solution of p-chlorophenol, dianhydride, boric acid and oleum is heated to a temperature of at least 175° C. while providing stirring. The reaction mixture is held at this temperature for a sufficient period of time to complete the reaction. Eight to ten hours is usually sufficient.

At the conclusion of the reaction, after cooling, the entire reaction mixture is poured into a large volume of water. The bis-quinizarin product is insoluble in water at pH 2 or less and can be boiled to aid in removing the excess dianhydride charged to the reaction mixture. Several washings should be made to obtain a product of high purity. In subsequent washings, a mineral acid such as sulfuric or hydrochloric should be added if required to maintain the pH below 2. Where a product of maximum purity is desired, the washed bis-quinizarin can be dissolved in dilute caustic solution and filtered. Acidification of the filtrate precipitates the bis-quinizarin.

The following example is set forth to illustrate the invention to those skilled in the art.

EXAMPLE 1

Part A

A three-necked flask, equipped with a mechanical stirrer, a thermometer, and a nitrogen inlet, was charged with approximately 325 grams of 10% oleum. There then was added to the reactor, in sequence over a period of approximately 5 minutes, 48.7 grams (0.379 mol) of p-chlorophenol, 70.7 grams (0.219 mol) of 3,3′4,4′-benzophenonecarboxylic acid (BTDA) and 33.6 grams (0.54 mol) of boric acid. At the conclusion of these additions, the temperature in the flask had increased to 78° C. The reaction mixture was heated to 190° C. over a period of 1.5 hours and then was maintained at a temperature of 188°–194° C. for an additional period of 9.5 hours. The reaction mixture was cooled to substantially ambient temperature, poured into 1300 ml of water, stirred for 15 minutes, and filtered. The precipitate was a very dark red color. The product was resuspended in an additional 1300 ml of water with stirring, heated to the boiling point for two hours, and again filtered. The product was again slurried in 1300 ml of water and boiled for an additional 30-minute period. The recovered dark red solid then was dissolved in 500 ml of 10% aqueous KOH to provide a solution which had a deep blue color. The alkaline solution was acidified with 100 ml of commercial grade concentrated hydrochloric acid to reprecipitate the product as a dark red solid. The product was filtered and washed with deionized water until the pH of the filtrate reached a value of 2.0. It was noted that as the pH approached 2.0, a portion of a solid material appeared to dissolve. The product was dried in a vacuum oven at 100° C. for 24 hours to obtain a yield of 77.8 grams (81% of theory) of the desired, 6,6′-carbonyl bis-quinizarin (CBQ). The product melted over a range of 272°–278° C.

An IR spectrum of the product showed no anhydride absorptions. A small aliquot of the product was dissolved in N-methyl-2-pyrrolidone (NMP) and separated into components by liquid chromatography employing a microporasil column. The product contained one main component and only trace amounts of three other components which were not identified.

Part B

Several attempts were made to prepare CBQ from the same reactants employed in Part A. The process conditions were essentially the same except that commercial grade concentrated sulfuric acid (98%) was employed in lieu of the oleum of Part A. The IR spectrum of the product obtained showed absorption bonds indicative of the presence of anhydride groups. A solution of the product in NMP was separated by liquid chromatography (using a microporasil column) into two major components, which were present in approximately equal amounts, and two minor components.

The bis-quinizarin compounds of the invention have intense colors and very limited solubility in hydrocarbon solvents. For these reasons, they have utility as organic pigments in surface coating compositions (paints, lacquers, and the like), resin compositions, printing inks, and the like. They can be employed as intermediates in the manufacture of dyes, antioxidants, and the like.

To prepare an attractive red colored polystyrene composition, one part of the CBQ particles of Example 1, Part A, can be dry blended with one thousand parts of a finely ground colorless polystyrene crystal containing about 0.2% stearic acid as a lubricant. The blending can be carried out in a conventional tumbling type blender. The mixture can be extruded at temperatures of about 450°–500° F. to form strands which then can be cut into pellets of a size suitable for use in an injection molding machine. Test molding specimens measuring 3″×7″×¼″ have an attractive red color.

The bis-quinizarin compounds contain structural groupings very similar to those present in quinizarin. They may be viewed as being made from two mols of quinizarin joined together through the X groups of the first formula set forth above. For this reason, they undergo virtually all of the known quinizarin reactions and produce useful and attractive dye stuffs. For a general review of the type of reactions possible, see Chapter XXIX of the text *The Chemistry of Synthetic Dyes* by K. Venkataraman, Volume II, Academic Press of New York, 1952, Library of Congress Catalog Card Number 52-5201. By way of specific example, when an aqueous solution of CBQ, sodium sulfite and copper oxide is boiled, the sodium salt of the bis-2-sulfonic acid is obtained in virtually a quantitative yield.

By employing conditions similar to those disclosed in British Pat. No. 419,954, it is possible to prepare an attractive dye by first condensing four mols of p-toluidine with CBQ, then oxidizing the vat mixture, and finally sulfonating the product. The structure of the sodium salt is believed to be:

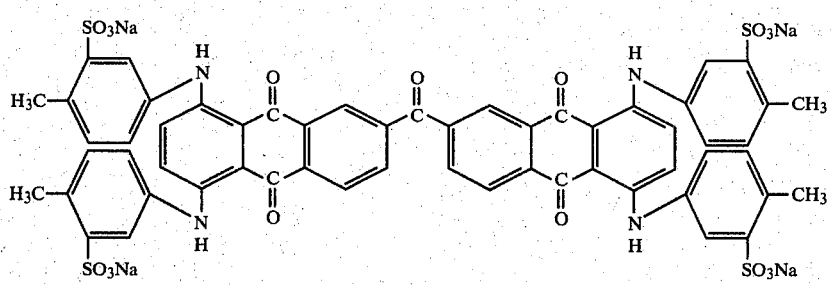

By an identical series of reactions, additional attractive dyes are prepared by substituting p-aminodiphenyl or 1,2,3,4-tetrahydro-2-naphthylamine for the p-toluidine.

What is claimed:

1. A bis-quinizarin compound having the structure:

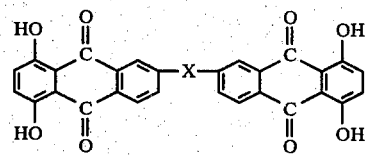

where X is

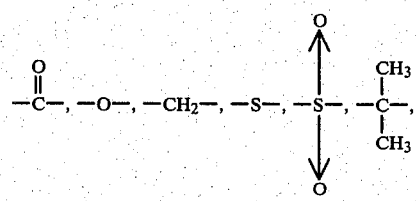

—CF$_2$—, or a direct bond.

2. 2,2'-carbonyl bis'-quinizarin having the structure:

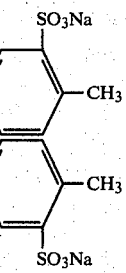

3. A process for preparing 6,6'-carbonyl bis-quinizarin (CBQ) which consists essentially of heating a reaction mixture containing 3,3',4,4'-benzophenonetetracarboxylic acid dianhydride (BTDA), p-chlorophenol, boric acid, and oleum to a temperature above 175° C. for a period of time sufficient to form CBQ, washing the reaction mixture with water to remove unreacted BTDA and recovering the CBQ; said reaction mixture (1) containing about 1.1 to 1.9 molar portion of p-chlorophenol per molar portion of BTDA, (2) containing at least 1 molar portion of boric acid per molar portion of p-chlorophenol, and (3) containing oleum in an amount of at least 200% of the combined weight of the BTDA and p-chlorophenol.

4. The process of claim 3 in which about 1.4 to 1.8 molar portion of p-chlorophenol is employed per molar portion of BTDA.

* * * * *